US012758259B2

(12) United States Patent
Yang

(10) Patent No.: US 12,758,259 B2
(45) Date of Patent: Oct. 13, 2026

(54) INSTALLATION UNIT OF ANALYTE DETECTION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 434 days.

(21) Appl. No.: 18/693,160

(22) PCT Filed: Jan. 30, 2022

(86) PCT No.: PCT/CN2022/075209
§ 371 (c)(1),
(2) Date: Mar. 19, 2024

(87) PCT Pub. No.: WO2023/045215
PCT Pub. Date: Mar. 30, 2023

(65) Prior Publication Data
US 2024/0400271 A1 Dec. 5, 2024

(30) Foreign Application Priority Data
Sep. 27, 2021 (WO) ................ PCT/CN2021/120858

(51) Int. Cl.
*A61B 17/34* (2006.01)
*A61B 5/145* (2006.01)

(52) U.S. Cl.
CPC ...... *A61B 17/3468* (2013.01); *A61B 5/14532* (2013.01); *A61B 2560/063* (2013.01)

(58) Field of Classification Search
CPC .......... A61B 5/14532; A61B 2560/063; A61B 17/3468; A61B 5/1473; A61B 5/14865
See application file for complete search history.

(56) References Cited

U.S. PATENT DOCUMENTS 6,385,878 B1 * 5/2002 Key ...................... G09F 3/0292 40/310
9,463,138 B2 * 10/2016 McClain .............. B65D 51/245
(Continued)

FOREIGN PATENT DOCUMENTS

CN 201676283 12/2010
CN 106137214 11/2016
(Continued)

OTHER PUBLICATIONS

"International Search Report (Form PCT/ISA/210) of PCT/CN2022/075209", mailed on Apr. 28, 2022, pp. 1-3.

*Primary Examiner* — Eric F Winakur
(74) *Attorney, Agent, or Firm* — JCIP GLOBAL INC.

(57) ABSTRACT

An installation unit of analyte detection device includes the housing, the protective cover and the label. The protective cover includes an outer cover and an inner cover. The outer ring of the label is fixed on the near end plane of the outer cover, the inner ring is fixed on the near end plane of the inner cover, and the inner ring of the label is connected with the outer ring through the easy tear seam. Before using the installation unit, the outer cover and inner cover remain fixed relative to the housing. When using the installation unit, the inner cover and inner ring of label remain fixed relative to the housing, and the outer cover and outer ring of label rotate relative to the housing to damage the easy tear seam.

12 Claims, 7 Drawing Sheets

(56) References Cited

U.S. PATENT DOCUMENTS

| | | | | |
|---|---|---|---|---|
| 2010/0187233 | A1* | 7/2010 | Fraser .................... | B65D 41/08<br>220/288 |
| 2021/0275066 | A1* | 9/2021 | Chae .................. | A61B 5/14532 |
| 2022/0225899 | A1* | 7/2022 | Peterson ............ | A61B 5/14532 |

FOREIGN PATENT DOCUMENTS

| | | |
|---|---|---|
| CN | 207029940 | 2/2018 |
| CN | 110720930 | 1/2020 |
| CN | 210149908 | 3/2020 |
| CN | 111588387 | 8/2020 |
| WO | 2021046255 | 3/2021 |

* cited by examiner

INSTALLATION UNIT OF ANALYTE DETECTION DEVICE

CROSS-REFERENCE TO RELATED APPLICATION

This application is a 371 application of the International PCT application serial no. PCT/CN2022/075209, filed on Jan. 30, 2022, which claims the priority benefit of the International PCT application no. PCT/CN2021/120858, filed on Sep. 27, 2021. The entirety of each of the above mentioned patent applications is hereby incorporated by reference herein and made a part of this specification.

TECHNICAL FIELD

The invention mainly relates to the field of medical devices, in particular to an installation unit of analyte detection device.

BACKGROUND

The pancreas in a normal human body can automatically monitor the blood glucose level and automatically secrete required amount of insulin/glucagon. In the body of a type 1 diabetes patient, the pancreas does not function properly and cannot produce enough insulin for the body. Therefore, type 1 diabetes is a metabolic disease caused by abnormal pancreatic function, and diabetes is a lifelong disease. At present, there is no cure for diabetes with medical technology. The onset and development of diabetes and its complications can only be controlled by stabilizing blood glucose.

Diabetics need to have their blood glucose measured before they inject insulin into the body. At present, most of the testing methods can continuously measure blood glucose level and transmit the data to a remote device in real time for the user to view. This method is called Continuous Glucose Monitoring (CGM).

However, the protective cover of the installation unit of the current analyte detection device cannot identify whether it has been opened after leaving the factory. If the protective cover has been opened, it may pollute the sensor or auxiliary needle of the sensor and affect the user experience.

Therefore, the prior art urgently needs an installation unit of the analyte detection device that can identify whether the protective cover has been opened.

BRIEF SUMMARY OF THE INVENTION

The invention discloses an installation unit of analyte detection device, which comprises the shell, the protective cover and the label. The protective cover comprises an outer cover and an inner cover. The outer ring of the label is fixed on the near end plane of the outer cover, the inner ring is fixed on the near end plane of the inner cover, and the inner ring of the label is connected with the outer ring through the easy tear seam. Before using the installation unit, the outer cover and inner cover remain fixed relative to the housing. When using the installation unit, the inner cover and inner ring of label remain fixed relative to the housing, and the outer cover and outer ring of label rotate relative to the housing to damage the easy tear seam. After the easy tear seam is damaged, it cannot be restored. The user can judge whether the protective cover of the installation unit has been opened through the state of the easy tear seam, so as to avoid using the contaminated analyte detection device.

The invention provides an installation unit of analyte detection device, which comprises: the protective cover, the protective cover comprises an outer cover and an inner cover, the outer cover comprises a near end plane of the outer cover, and the inner cover comprises a near end plane of the inner cover; The label, which comprises an inner ring and an outer ring, the inner ring is fixed on the near end plane of the inner cover, and the inner ring and the outer ring are connected through the easy tear seam; And the housing, before using the installation unit, the protective cover is fixedly connected with the housing; When using the installation unit, the inner cover remains stationary relative to the housing, the outer cover rotates relative to the housing to damage the easy tear seam at the same time.

According to one aspect of the invention, the housing is provided with the chute, correspondingly, the outer cover is provided with the bump, which can rotate into or out of the chute.

According to one aspect of the invention, when the bump rotates into the chute, the outer cover is fixed with the housing, when the bump rotates out of the chute, the outer cover is separated from the housing.

According to one aspect of the invention, the triggering module is also fixed in the housing, and the fixed groove is arranged on the triggering module, correspondingly, the inner cover is provided with the rib. Before using the installation unit, the rib is located in the fixed groove.

According to one aspect of the invention, the outer cover is also provided with the punctate bulge, and the inner cover is also provided with the annular bulge, which is located between the punctate bulge and the near end plane of the outer cover.

According to one aspect of the invention, the number of chutes shall be at least two, which are symmetrically distributed on the housing.

According to one aspect of the invention, the number of chutes is three, with the interval of 120° between each other.

According to one aspect of the invention, the number of fixed grooves shall be at least two, which are symmetrically distributed on the triggering module.

According to one aspect of the invention, the number of fixed grooves is three, with an interval of 120° between each other.

According to one aspect of the invention, the number of punctate bulges is at least two, which are symmetrically distributed on the outer cover.

According to one aspect of the invention, the number of punctate bulges is three, with an interval of 120° between each other.

According to one aspect of the invention, the label is made of paper or plastic.

Compared with the prior art, the technical scheme of the invention has the following advantages:

The installation unit of the analyte detection device disclosed by the invention comprises the shell, the protective cover and the label. The protective cover comprises an outer cover and an inner cover. The outer ring of the label is fixed on the near end plane of the outer cover, the inner ring is fixed on the near end plane of the inner cover, and the inner ring of the label is connected with the outer ring through an easy tear seam. Before using the installation unit, the outer cover and inner cover remain fixed relative to the housing. When using the installation unit, the inner cover and label inner ring remain fixed relative to the housing, and the outer cover and outer ring of label rotate relative to the housing, which could damage the easy tear seam. After the easy tear seam is damaged, it cannot be restored. The user can judge whether the protective cover of the installation unit has been opened through the state of the easy tear seam, so as to avoid using the contaminated analyte detection device.

Further, the bump on the outer cover rotates into or out of the chute on the housing to realize the connection or separation between the outer cover and the housing.

Further, the outer cover restricts the annular bulge of the inner cover through the punctate bulge and the near end plane of the outer cover, so that the inner cover can rotate relative to the outer cover without separating from the outer cover. When the outer cover is separated from the housing, the inner cover can also be separated from the housing, with simple structure and convenient processing.

Further, the triggering module restricts the ribs of the inner cover through the fixed groove. When the outer cover rotates, the inner cover does not rotate together, which is convenient to damage the easy tear seam of the label. The structure is simple and convenient for processing.

Further, the label is made of paper or plastic, which is easy to process and damage the easy tear seam.

DETAILED DESCRIPTION

As mentioned above, the protective cover of the installation unit of the existing analyte detection device cannot identify whether it has been opened after leaving the factory. If the protective cover has been opened, it may cause external dirt to pollute the sensor or auxiliary needle of the sensor and affect the user experience.

In order to solve this problem, the invention provides an installation unit of analyte detection device, which comprises the housing, the protective cover and the label. The protective cover comprises an outer cover and an inner cover. The outer ring of the label is fixed on the near end plane of the outer cover, the inner ring is fixed on the near end plane of the inner cover, and the inner ring of the label is connected with the outer ring through the easy tear seam. Before using the installation unit, the outer cover and inner cover remain fixed relative to the housing. When using the installation unit, the inner cover and label inner ring remain fixed relative to the housing, and the outer cover and outer ring of the label rotate relative to the housing, which could damage the easy tear seam. After the easy tear seam is damaged, it cannot be restored. The user can judge whether the protective cover of the installation unit has been opened through the state of the easy tear seam, so as to avoid using the contaminated analyte detection device.

Various exemplary embodiments of the invention will now be described in detail with reference to the attached drawings. It is understood that, unless otherwise specified, the relative arrangement of parts and steps, numerical expressions and values described in these embodiments shall not be construed as limitations on the scope of the present invention.

In addition, it should be understood that the dimensions of the various components shown in the attached drawings are not necessarily drawn to actual proportions for ease of description, e. g. the thickness, width, length or distance of some elements may be enlarged relative to other structures.

The following descriptions of exemplary embodiments are illustrative only and do not in any sense limit the invention, its application or use. Techniques, methods and devices known to ordinary technicians in the relevant field may not be discussed in detail here, but to the extent applicable, they shall be considered as part of this manual.

It should be noted that similar labels and letters indicate similar items in the appending drawings below, so that once an item is defined or described in one of the appending drawings, there is no need to discuss it further in the subsequent appending drawings.

Figure 1:
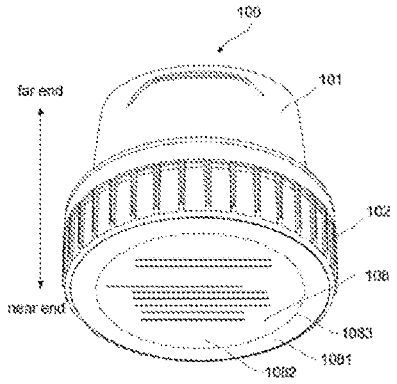
FIG. 1 is the schematic diagram of the external structure of the installation unit of the analyte detection device according to an embodiment of the invention.

FIG. 1 is the schematic diagram of the external structure of the installation unit of the analyte detection device according to an embodiment of the invention. The external structure of the installation unit 100 comprises the housing 101 for carrying internal structural members and the protective cover 102. When the installation unit 100 is in use, the end close to the user's skin is the near end, and the end away from the skin is the far end. A first opening is arranged in the near end of the housing 101. When using the installation unit, the analyte detection device is installed on the surface of the user's skin from the first opening. The protective cover 102 is located in the first opening for protecting, sealing and anti-triggering the interior of the housing 101, such as protecting the sensor and auxiliary needle of the analyte detection device, anti-triggering the triggering module, etc.

External Structure of the Housing

Figure 2A:
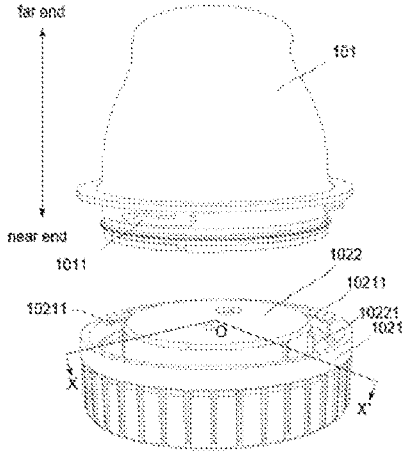
FIG. 2*a* is the structural diagram of the separation of the shell and the protective cover according to an embodiment of the invention.
Figure 2B:
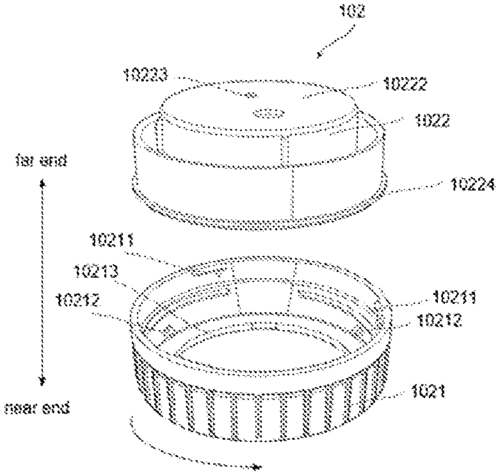
FIG. 2*b* is the schematic diagram of the protective cover according to an embodiment of the invention.
Figure 2C:
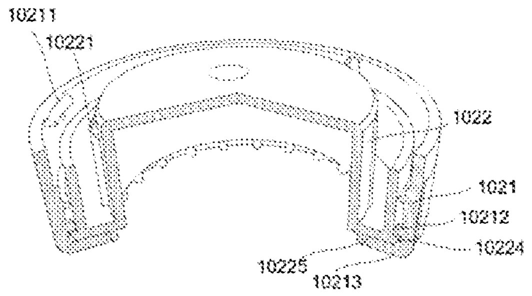
FIG. 2*c* is the structural diagram of x-x' section in FIG. 2*a;*

FIG. 2*a* is the structural diagram of the separation of the housing and the protective cover according to an embodiment of the invention; FIG. 2*b* is the structural diagram of the protective cover; FIG. 2*c* is the structural diagram of section x-x' in FIG. 2*a*.

With reference to FIGS. 2*a*, 2*b* and 2*c*. In the embodiment of the invention, the protective cover 102 comprises an outer cover 1021 and an inner cover 1022. The second opening is arranged in the far end of the outer cover 1021, and the second opening is opposite to the first opening.

In the embodiment of the invention, the punctate bulge 10212 is arranged on the inner side of the outer cover 1021, the annular bulge 10224 is arranged on the outer side of the inner cover 1022, and the annular bulge 10224 surrounds the outer side of the inner cover at 360°. The inner cover 1022 can be assembled on the inner side of the outer cover 1021 through the annular bulge 10224. Specifically, the annular bulge 10224 is embedded between the punctate bulge 10212 and the near end plane 10213 of the outer cover, so that the inner cover 1022 can only rotate in the outer cover 1021 and cannot be separated from the outer cover 1021.

In the embodiment of the invention, the number of punctate bulges 10212 is at least two, which are symmetrically distributed on the inner side of the outer cover 1021, and the annular bulges 10224 can be stably limited in the outer cover 1021. In the preferred embodiment of the invention, the number of punctate bulges 10212 is three, which are distributed on the inner side of the outer cover 1021 at 120° to each other.

In the embodiment of the invention, the bump 10211 is also arranged on the inner side of the outer cover 1021. Correspondingly, the chute 1011 is arranged on the outer side of the housing 101. The bump 10211 can slide and insert into the chute 1011 by rotating, so that the outer cover 1021 is assembled on the housing 101 and fixed with the housing 101. Here, "corresponding" indicates that the number and spacing angle of bump 10211 are consistent with chute 1011.

In the embodiment of the invention, there are at least two bumps 10211 symmetrically distributed on the outer cover 1021. In the preferred embodiment of the invention, the number of bumps 10211 is three, and the spacing angle between them is 120°.

In the embodiment of the invention, the near end of the outer cover 1021 also comprises the near end plane 10213 of the outer cover, and the near end plane 10225 of the inner cover 1022. The near end plane 10213 of the outer cover is located on the same side as the near end plane 10225 of the inner cover 1022.

Referring to FIG. 1, in the embodiment of the present invention, the label 108 is also arranged on the near end plane 10213 of the outer cover and the near end plane 10225 of the inner cover. The label 108 comprises an outer ring 1081 and an inner ring 1082. The outer ring 1081 and the inner ring 1082 are combined into a whole through the easy tear seam 1083, and are respectively pasted and fixed on the near end plane 10213 of the outer cover and the near end plane 10225 of the inner cover. In the embodiment of the invention, the outer ring 1081 is fixed on the near end plane 10213 of the outer cover, and the inner ring 1082 is fixed on the near end plane 10225 of the inner cover.

In the embodiment of the invention, the label 108 is a paper or plastic product, so as to facilitate the processing of the easy tear seam 1083 between the outer ring 1081 and the inner ring 1082, and the easy tear seam 1083 is easy to be damaged.

In the embodiment of the invention, text information can also be printed on the outer ring 1081 or inner ring 1082, such as the use method of the installation unit or analyte detection device, the calibration free code of the sensor, the production date, etc.

In the embodiment of the invention, the rib 10221 is also arranged on the inner cover 1022, and the rib 10221 is vertically arranged relative to the near end plane 10225 of the inner cover.

Figure 8A:
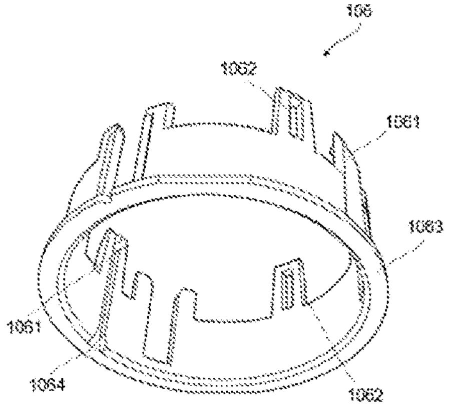
FIG. 8*a* is the schematic diagram of the triggering module according to an embodiment of the invention.
Figure 8B:
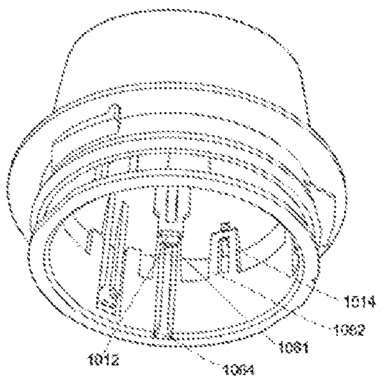
FIG. 8*b* is the structural diagram of the triggering module installed on the housing according to an embodiment of the present invention.

Referring to FIG. 8*b*, in the embodiment of the present invention, before using the installation unit 100, the protective cover 102 is installed on the housing 101, the bump 10211 on the outer cover 1021 rotates into the chute 1011, and the rib 10211 enters the fixed groove 1064 of the triggering module 106. Due to the restriction of the fixed groove 1064 on the rib 10211 and the restriction of the punctate bulge 10212 on the annular bulge 10224, the inner cover 1022 and the label inner ring 1082 fixed on the inner cover 1022 cannot move relative to the housing 101. As a whole, the protective cover 102 is fixedly connected with the housing 101.

When using the installation unit 100, one hand of user holds the housing 101 and the other holds the outer cover 1021, rotates the outer cover 1021, the bump 10211 rotates out of the chute 1011, the outer cover 1021 is separated from the housing 101, the rib 10221 of the inner cover 1022 is still located in the fixed groove 1064 of the triggering module 106, and the inner cover 1022 remains stationary relative to the housing 101. At the same time, the outer ring 1081 of the label rotates relative to the inner ring 1082, and the easy tear seam 1083 is damaged. After the easy tear seam 1083 is damaged, it cannot be restored. The user can judge whether the installation unit 100 has been used according to the use of the easy tear seam 1083.

Internal Structure of the Housing

Figure 3:
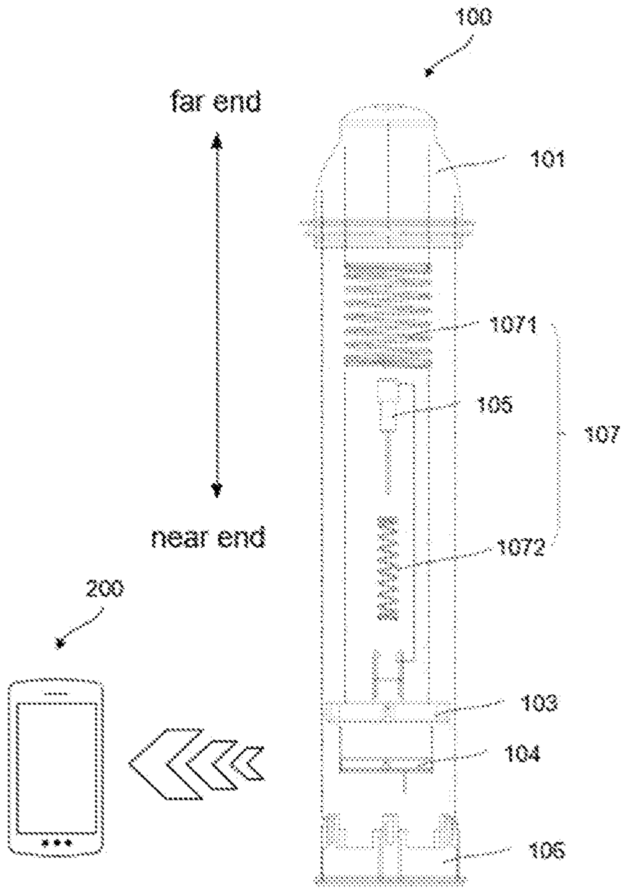
FIG. 3 is the schematic diagram of the explosive structure of the installation unit of the analyte detection device according to an embodiment of the invention.

FIG. 3 is the schematic diagram of explosive structure of the installation unit of analyte detection device in embodiment of the present invention, and the dotted line in the figure represents the installation and coordination relationship of each structural component. The internal structure of installation unit 100 of the analyte detection device comprises parallel slider module 103, analyte detection device 104, auxiliary-needle module 105, triggering module 106 and elastic module 107, which comprises the first elastic component 1071 and the second elastic component 1072.

Figure 4:
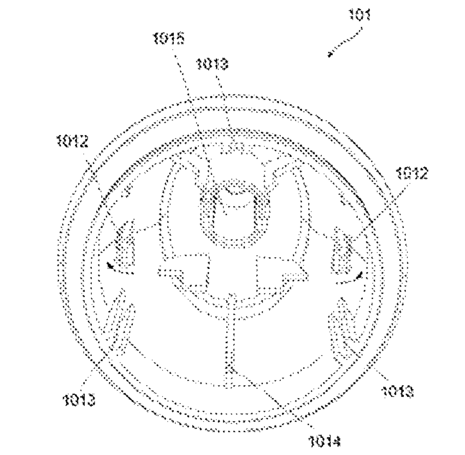
FIG. 4 is the schematic diagram of the internal structure of the housing according to an embodiment of the invention.

FIG. 4 is the schematic diagram of the internal structure of housing 101 in embodiment of the invention.

In an embodiment of the invention, at least two first buckles 1012 are arranged in the housing 101. The first buckle 1012 is integrated with the housing 101 and protrudes toward the near end of the housing 101. The first buckle 1012 is of flexible material and its end can be bent towards the outside of the housing 101.

In the preferred embodiment of the invention, the number of the first buckle 1012 is two, symmetrically distributed inside the housing 101, and the angle interval between each other is 180°.

In other preferred embodiments of the invention, the number of the first buckle 1012 is three or four, symmetrically distributed inside the housing 101, and the angle interval between them is 120° or 90°. The number of the first buckle 1012 can also be five or more, there is no limit here.

In the embodiment of the invention, housing 101 is also provided with at least two limit slots 1013, at least two slots 1014 and an auxiliary-needle limit slot 1015.

In an embodiment of the present invention, the limit slot 1013 comprises at least two ribbed plates projecting from the inner wall of housing 101. In preferred embodiments of the invention, the ribbed plates are parallel to each other and grooves are formed in the middle of adjacent ribbed plates.

In other embodiments of the invention, the limit slot 1013 is a slot that is sunken into the inner wall of housing 101.

Figure 10A:
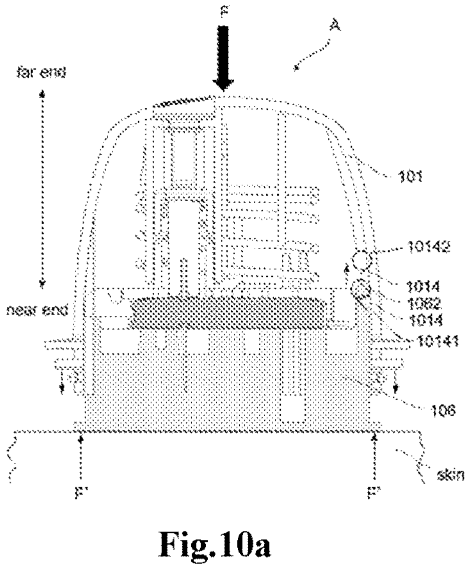
FIG. 10*a* is the schematic diagram of section A structure in FIG. 9.

In the embodiment of the present invention, slot 1014 comprises two slot points, namely, the first slot point 10141 and the second slot point 10142, as shown in FIG. 10*a*, the first slot point 10141 is closer to the near end relative to the second slot point 10142.

In the preferred embodiment of the invention, there are two limit slots 1013 and slots 1014, which are symmetrically distributed inside the housing 101 with an angle interval of 180° between them.

In other preferred embodiments of the invention, there are three or four limit slots 1013 and slots 1014, which are symmetrically distributed inside housing 101 with an angle interval of 120° or 90° between them. The number of limit slots 1013 and slots 1014 can also be five or more, there is no limit here.

Parallel Slider Module

Figure 5A:
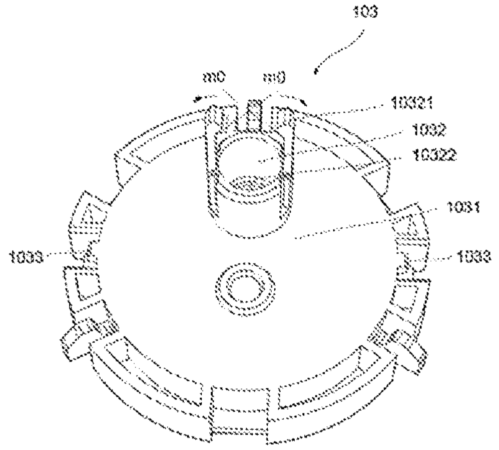
FIG. 5*a* is a structural schematic diagram of the far end of the parallel slider module according to an embodiment of the invention.
Figure 5B:
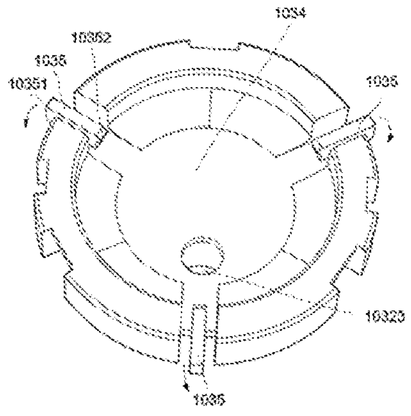
FIG. 5*b* is a structural schematic diagram of the near end of the parallel slider module according to an embodiment of the invention.

FIG. 5*a* is the structural diagram of the far end plane of parallel slider module 103, and FIG. 5*b* is the structural diagram of the near end plane of parallel slider module 103.

In the embodiment of the invention, the far end plane 1031 of the parallel slider module 103 is provided with a circular groove 1032 that protrudes to the far end. The circular groove 1032 is an internal hollowed cylindrical structure, and its inner diameter is d1. At least two slide-buckle 10321 are extended from the side wall of circular groove 1032 to the far end. The buckle part of the slide-buckle 10321 is plane or nearly plane, and is at a fixed angle with the horizontal plane, and its extended end m0 converges at the far end.

In an embodiment of the invention, the slide-buckle 10321 is a flexible material and can therefore be bent to the outside of the circular groove 1032.

In other embodiments of the invention, the slide-buckle 10321 may be directly arranged on the far end plane of the parallel slider module 103 without the need for a circular groove structure.

In the embodiment of the invention, the end of the circular groove 1032 near the far end plane 1031 is also provided with a bump 10322. The bump 10322 is an internally hollowed-out cylindrical structure with an inner diameter of d2, which can be understood as d1>d2. The circular groove 1032 of the internal hollowed out structure and the bump 10322 form a through hole 10323, which penetrates from the far end plane 1031 of the parallel slider module to the near end plane 1034.

In the preferred embodiment of the invention, the number of slide-buckle 10321 is two, symmetrically distributed on the side wall of circular groove 1032, and the angle interval between the two slide-buckle 10321 is 180°.

In other preferred embodiments of the invention, the number of slide-buckles 10321 can be three or four, symmetrically distributed on the side wall of circular groove 1032, and the angle interval between slide-buckles 10321 is 120° or 90°. The number of slide-buckles 10321 can also be five or more, there is no limit here.

According to FIG. 5*a*, in an embodiment of the invention, at least two second buckles 1033 are arranged on the side of the far end plane 1031 of parallel slider module 103. The second buckles 1033 are symmetrically distributed on the side of 1031 on the far end plane with an angle interval of 180° between them.

In other embodiments of the invention, the number of the second buckles 1033 is three or four, symmetrically distributed on the side of the far end plane 1031, and the angle interval between them is 120° or 90°. The number of the second buckles 1033 can also be five or more, there is no limit here. In installation unit 100, the second buckle 1033 is coupled to the first buckle 1012. The position and number of the second buckle 1033 is the same as the first buckle 1012.

According to FIG. 5*b*, in the embodiment of the present invention, at least two T-shaped structure 1035 are arranged on the side of the near end plane 1034 of parallel slider module 103. The vertical part of T-shaped structure 1035 is connected to the near end plane 1034, and the horizontal part comprises T-shaped-structure slider 10351 and T-shaped-structure buckle 10352. The T-shaped-structure slider 10351 is oriented to the outside of the parallel slider module 103 and protrudes out of the outer ring of the parallel slider module 103; T-shaped-structure buckle 10352 faces the inside of the parallel slider module 103 and protrudes from the inner ring of the parallel slider module 103.

In installation unit 100, T-shaped-structure slider 10351 is located in limit slot 1013 to limit the position of parallel slider module 103 and prevent rotation of parallel slider module 103. The number and position of T-shaped-structure slider 10351 are the same as that of limit slot 1013. In the process of moving the parallel slider module 103 towards the near end, the T-shaped-structure slider 10351 slides in the limit slot 1013.

In the preferred embodiment of the invention, the vertical part of T-shaped structure 1035 is a flexible material, the vertical part and the horizontal part are formed in one piece, and thus the horizontal part can be bent around the vertical part.

In other preferred embodiment of the invention, the vertical part of T-shaped structure 1035 is elastic material, such as spring, shrapnel, etc., and the horizontal part is fixedly connected with the vertical part through welding or hot melting processes, and the horizontal part can also be bent around the vertical part.

Analyte Detection Device

Figure 6:
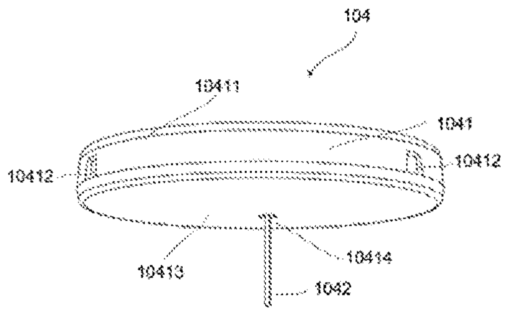
FIG. 6 is the schematic diagram of the analyte detection device according to an embodiment of the invention.

FIG. 6 is the schematic diagram of the analyte detection device in an embodiment of the present invention.

In combination with FIG. 3, in an embodiment of the present invention, the analyte detection device 104 comprises a shell 1041, a transmitter (not shown in the figure), a sensor 1042 and an internal circuit (not shown in the figure) arranged in the shell 1041 which electrically couples with the sensor. Sensor 1042 is used to detect the parameter information of user's body fluid analyte, and transmits the parameter information of the analyte to the transmitter through the internal circuit, and then from the transmitter to the external equipment 200.

In the preferred embodiment of the invention, before the analyte detection device 104 is installed on the user's skin surface, the signal is transmitted to the external device 200 at the first frequency $f_1$, and after it is installed on the user's skin surface, the signal is transmitted to the external device 200 at the second frequency $f_2$, and the second frequency $f_2$ is greater than the first frequency $f_1$. In further preferred embodiments of the invention, the first frequency $f_1$ is 0~12 times/hour and the second frequency $f_2$ is 12~3600 times/hour.

In the preferred embodiment of the invention, the first frequency $f_1$ is 0 times/hour, that is, before the analyte detection device 104 is installed on the user's skin surface, no signal is transmitted to the external device 200, so as to save the power consumption of the analyte detection device 104 before installation.

In an embodiment of the invention, the shell 1041 comprises an upper-outer-shell 10411 and a lower-outer-shell 10413, and the upper-outer-shell 10411 and the lower-outer-shell 10413 are spliced together to form an internal space.

The sensor 1042 consists of an external part (not shown in the figure) and an internal part (not shown in the figure). The external part, the transmitter and the internal circuit are arranged in the internal space and the external part is electrically coupled to the internal circuit. The internal part is provided with electrodes, membranes and other structures, which can be inserted into the user's skin to detect the parameters of the analyte. When the internal part is inserted under the skin, it needs to be inserted at the correct angle, such as perpendicular to the skin surface. At the end of its life, the analyte detection device 104 is removed from the user's skin surface and discarded as a whole.

In the embodiment of the invention, the lower-outer-shell 10413 comprises the first through-hole 10414. Correspondingly, on the axis of the first through-hole 10414, the upper-outer-shell 10411 comprises the second through-hole (not shown in the figure), and the internal part passes through the first through-hole 10414 to the outside of the shell, so as to penetrate the user's subcutaneous skin.

In the embodiment of the invention, the side of the upper-outer-shell 10411 comprises buckle hole 10412 corresponding to T-shaped-structure buckle 10352, there "corresponding" means that the position and number of buckle hole 10412 are consistent with that of T-shaped-structure buckle 10352. In the installation unit 100, the upper-outer-shell 10411 is fitted with the near end plane 1034, the T-shaped-structure buckle 10352 forms a buckle-connection with the buckle hole 10412, and the analyte detection device 104 is fixed on the parallel slider module 103. When the horizontal part of the T-shaped structure 1035 is bent around the vertical part, the buckle-connection between the T-shaped-structure buckle 10352 and the buckle hole 10412 is removed, and the analyte detection device 104 is separated from the parallel slider module 103. Therefore, in installation unit 100, analyte detection device 104 and parallel slider module 103 are releasable connection.

Auxiliary-Needle Module

Figure 7:
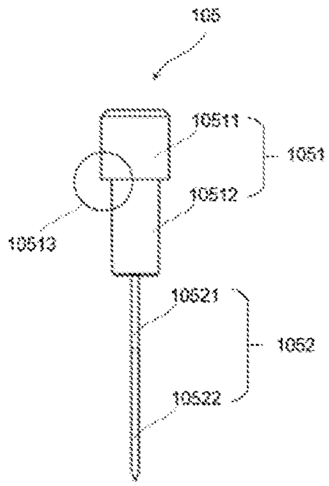
FIG. 7 is the schematic diagram of the auxiliary-needle module according to an embodiment of the invention.

FIG. 7 is the schematic diagram of the auxiliary-needle module in an embodiment of the invention.

In an embodiment of the invention, the auxiliary-needle module 105 comprises an auxiliary-needle fixed structure 1051 and an auxiliary-needle 1052. In the installation unit 100, the auxiliary-needle fixed structure 1051 is located at the far end relative to the auxiliary-needle 1052.

In the embodiment of the invention, the auxiliary-needle fixed structure 1051 comprises an auxiliary-needle slide block 10511 and an auxiliary-needle fixed block 10512. The diameter or width of the auxiliary-needle slide block 10511 is larger than that of the auxiliary-needle fixed block 10512, forming a convex surface 10513 toward the near end.

In the embodiment of the invention, the auxiliary-needle 1052 comprises a fully-enclosed needle body 10521 and a semi-enclosed needle body 10522. The fully-enclosed needle body 10521 is located between the auxiliary-needle fixed block 10512 and the semi-enclosed needle body 10522, and is fixedly connected with the auxiliary-needle fixed block 10512. The hollow structure of the semi-enclosed needle 10522 can be used to accommodate the internal part of the sensor 1042. When the semi-enclosed needle 10522 is inserted into the user's skin, the internal part can be also inserted into the user's skin, and the state of the internal part is not affected when the needle is retracted.

In other embodiments of the invention, the auxiliary-needle 1052 only comprises the semi-enclosed needle body 10522, that is, the semi-enclosed needle body 10522 is fixedly connected with the auxiliary-needle fixed block 10512, which can reduce the material used for the auxiliary-needle 1052 and save costs, but also reduce the rigidity of the auxiliary-needle 1052.

In installation unit 100, auxiliary-needle 1052 passes through the second through-hole and the first through-hole 10414 successively, thus passing through analyte detection device 104. The internal part of sensor 1042 is located in semi-enclosed needle body 10522.

Triggering Module

FIG. **8*a* is the structural diagram of the triggering module according to an embodiment of the present invention; FIG. 8*b*** is the structural diagram of the triggering module installed on the housing according to an embodiment of the invention.

With reference to FIGS. **8*a* and 8*b***.

In an embodiment of the invention, the triggering module 106 is provided with at least two fixed buckle 1061 corresponding to the first buckle 1012. In installation unit 100, the fixed buckle 1061 is in contact with the first buckle 1012 to prevent the first buckle 1012 from bending to the outside of the housing 101. The contact between the fixed buckle 1061 and the first buckle 1012 can be point-contact, line-contact or surface-contact. When the contact is surface-contact, the contact surface between the fixed buckle 1061 and the first buckle 1012 is at a fixed angle with the horizontal plane and converges at the near end of the installation unit 100. The number and position of the fixed buckle 1061 is the same as the first buckle 1012.

In the embodiment of the invention, there are also at least two lugs 1062 arranged on the triggering module 106. In the installation unit 100, the lug 1062 and the slot 1014 snap together to fix the triggering module 106. The number and position of lug 1062 are the same as slot 1014. According to FIG. **10*a*, before installation unit 100 is used, lug 1062 is located in slot 10141 of the first buckle. At this point, the fixed buckle 1061 is in contact with the first buckle 1012**.

In the embodiment of the invention, the triggering module 106 is also provided with the fixed groove 1064, which corresponds to the rib 10221 of the inner cover 1022. When the protective cover 102 is installed on the housing 101, the rib 10221 enters into the fixed groove 1064.

In the embodiment of the invention, the fixed groove 1064 is located at the same position as the fixing buckle 1061, so that the fixed groove 1064 can have sufficient length to accommodate the rib 10221.

In the embodiment of the invention, the number of fixed groove 1064 is consistent with the number of rib 10221. In the preferred embodiment of the invention, the number of fixed grooves 1064 is three, which are distributed on the triggering module at an interval of 120° with each other.

In an embodiment of the invention, the triggering module 106 also comprises the fixed ring 1063, which connects the fixed buckle 1061 and the lug 1062 into an integral whole. In installation unit 100, the fixed ring 1063 is proximal to the first opening and protrudes from the first opening relative to the lug 1062. In using installation unit 100, the fixed ring 1063 is attached to the user's skin surface.

Elastic Module

According to FIG. 3, the elastic module 107 comprises the first elastic component 1071 and the second elastic component 1072.

In the embodiment of the invention, the first elastic component 1071 is located between the parallel slider module 103 and the housing 101, that is, one end of the first elastic component 1071 is located on the far end plane of the parallel slider module 103, and the other end is located in the housing 101. In the installation unit 100, the first elastic component 1071 is in compression state and can provide elasticity.

In the embodiment of the invention, the second elastic component 1072 is located between parallel slider module 103 and auxiliary-needle module 105, that is, one end of the second elastic component 1072 is located on the bump 10322 of parallel slider module 103 and the other end is located on the convex surface 10513 of auxiliary-needle module 105. In the installation unit 100, the second elastic component 1072 is in a compressed state to provide elasticity.

In the preferred embodiment of the invention, the first elastic component 1071 or the second elastic component 1072 is a metal spring.

In the embodiment of the invention, the inner ring diameter of the first elastic component 1071 is larger than the outer ring diameter of the circular groove 1032 and the auxiliary-needle slide block 10511. In the installation unit 100, the first elastic component 1071 is surrounded by the outer side of the auxiliary-needle slide block 10511 and the circular groove 1032, so that the internal space of the installation unit 100 can be fully utilized.

In the embodiment of the invention, the outer ring diameter of the second elastic component 1072 is larger than the outer diameter of the auxiliary-needle fixed block 10512 and the inner diameter of the bump 10322, but smaller than the outer diameter of the auxiliary-needle slide block 10511 and the inner diameter of the circular groove 1032. Therefore, one end of the second elastic component 1072 is placed in the circular groove 1032. The other end is enclosed outside the auxiliary pin fixing block 10512 to make full use of the internal space of the installation unit 100.

Use Method of Installation Unit

Figure 9:
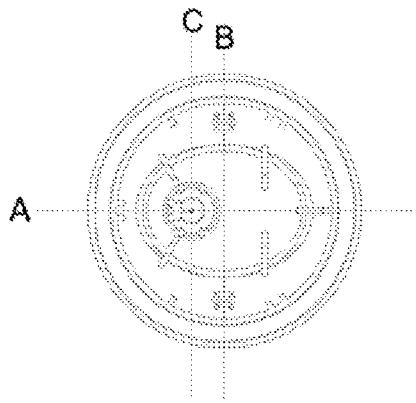
FIG. 9 is a top view of the installation unit according to an embodiment of the invention.

FIG. 9 is the top view of the installation unit of the embodiment of the invention.

FIG. 10*a* is the schematic diagram of section A structure in FIG. 9.

Figure 10B:
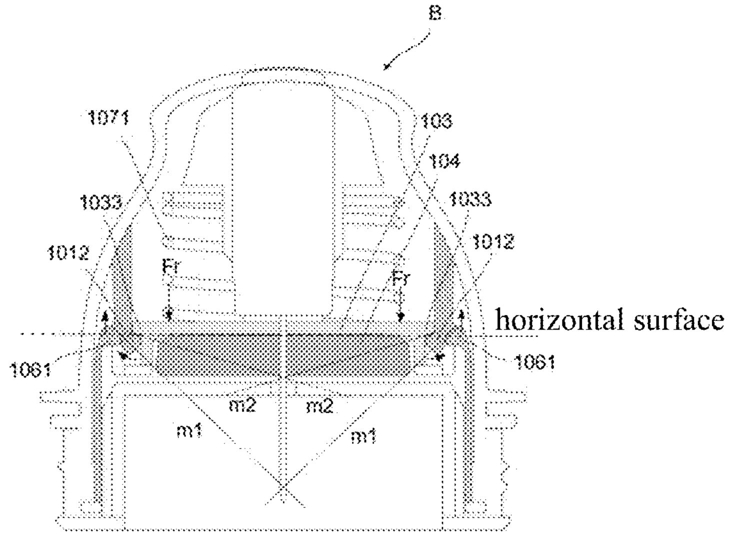
FIG. 10*b* is the schematic diagram of section B structure in FIG. 9.

FIG. 10*b* is the schematic diagram of section B structure in FIG. 9.

Figure 10C:
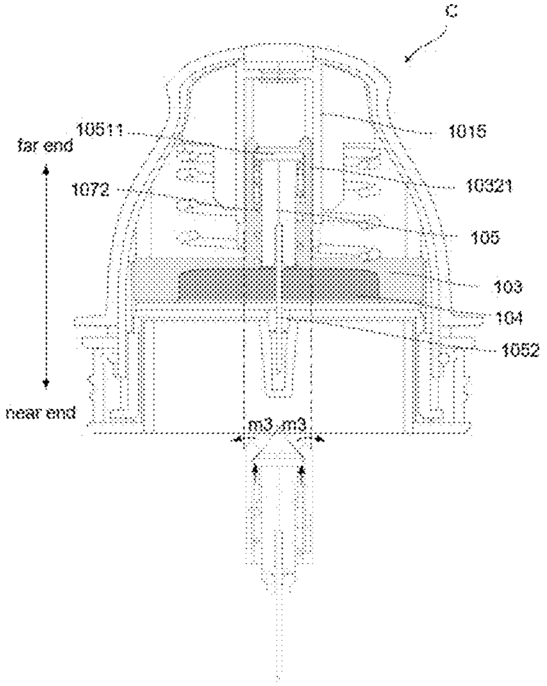
FIG. 10*c* is the schematic diagram of section C structure in FIG. 9.

FIG. 10*c* is the schematic diagram of section C structure in FIG. 9.

Figure 11:
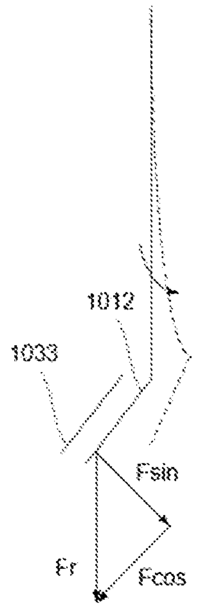
FIG. 11 is the bending schematic diagram of the first buckle because of force according to an embodiment of the invention.

FIG. 11 shows the bending diagram of the first buckle.

According to FIG. 10*a* and FIG. 10*b*, in the embodiment of the present invention, the slot 1014 is provided with the first slot point 10141 and the second slot point 10142. Before the installation unit 100 is used, triggering module 106 is fixed to the housing 101 through the coupling of lug 1062 and slot 10141, at this time, the fixed buckle 1061 is in contact with the first buckle 1012 to prevent the first buckle 1012 from bending to the outside of the housing 101. The fixed buckle 1061, the first buckle 1012 and the second buckle 1033 are at the same horizontal plane. In the preferred embodiment of the invention, the second buckle 1033, the first buckle 1012 and the fixed buckle 1061 are successively arranged from the housing 101 inside out.

In the embodiment of the invention, the contact between the fixed buckle 1061 and the first buckle 1012 is one of point-contact, line-contact or surface-contact. When the above contact is surface-contact, the extension line m1 of the contact surface converging at the near end. This kind of structural design can make the fixed buckle 1061 move toward the far end relative to the first buckle 1012.

In the preferred embodiment of the invention, the coupling surface of the second buckle 1033 and the first buckle 1012 is a plane, which has a fixed angle with the horizontal plane, and its extended line m2 converges at the near end.

With reference to FIG. 11, this kind of structural design can make the second buckle 1033 move toward the near end relative to the first buckle 1012, and push the first buckle 1012 toward the outside of the housing 101, so as to release the coupling state between the first buckle 1012 and the second buckle 1033.

In an embodiment of the invention, the first elastic component 1071 is in a state of compression and has elastic potential energy, and its self-elasticity gives thrust Fr to the near end of parallel slider module 103. The thrust Fr acts on the first buckle 1012 through the coupling surface of the second buckle 1033 and the first buckle 1012. And generate a component force F sin perpendicular to the plane of the first buckle 1012, which can push the first buckle 1012 toward the outside of the housing 101 to bend, so as to release the coupling state of the first buckle 1012 and the second buckle 1033.

In the embodiment of the invention, when the installation unit 100 is used, the outer cover 1021 is rotated to break the column 10211, the protective cover 102 is separated from the housing 101, and the near end of the installation unit 100 is close to the user's skin until the fixed ring 1063 of triggering module 106 is triggered to stick to the skin surface, and the user presses the housing 101 at the far end. The housing 101 moves toward the skin, while the triggering module 106 remains stationary. Therefore, the triggering module 106 moves toward the far end relative to the housing 101, and the lug 1062 disconnects from the first slot point 10141 and enters the second slot point 10142. Meanwhile, the fixed buckle 1061 no longer contacts with the first buckle 1012. The coupling state between the first buckle 1012 and the second buckle 1033 is released due to the bending of the component force F sin toward the outside of the housing 101.

In the embodiment of the invention, after the coupling state is released, the parallel slider module 103 continues to move toward the near end under the elastic force of the first elastic component 1071, and drives the analyte detection device 104 to move toward the near end until the lower-outer-shell 10413 of the analyte detection device 104 contacts the user's skin surface.

According to FIG. 10*c*, in the embodiment of the invention, the slide-buckles 10321 is connected with the auxiliary-needle slide block 10511. When the first elastic component 1071 pushes the parallel slider module 103 to move toward the near end, the auxiliary-needle module 105 is driven to move toward the near end together.

In an embodiment of the invention, the connection point of slide-buckles 10321 and auxiliary-needle slide block 10511 is a plane or approximate plane, which has a fixed angle with the horizontal plane, and the extension line m3 converges at the far end. The thrust force of the second elastic component 1072 on the auxiliary-needle slide block 10511 is toward the far end, so the auxiliary-needle slide block 10511 can push the slide-buckles 10321 toward the outside of the housing 101, making the slide-buckles 10321 bend, the principle of which is equivalent to FIG. 11.

In the embodiment of the invention, in the installation unit 100, the side wall of the limit slot 1015 of the auxiliary needle prevents the slide-buckles 10321 from bending, and the connection state of the slide-buckles 10321 and the auxiliary-needle slide block 10511 clasp does not change. As parallel slider module 103 and auxiliary-needle module 105 move towards the near end, the slide-buckles 10321 is separated from the auxiliary-needle limit slot 1015, and the inner wall of the auxiliary-needle limit slot 1015 no longer prevents the slide-buckles 10321 from bending. The second elastic component 1072 pushes the auxiliary-needle slide block 10511 to the far end. At the same time, the auxiliary-needle slide block 10511 pushes the slide-buckle 10321 to bend outwards, and the connection between the slide-buckle 10321 and the auxiliary-needle slide block 10511 is released. The second elastic component 1072 continues to push the auxiliary-needle slide block 10511 to move toward the far end, and finally the auxiliary-needle module 105 returns to its initial position. Auxiliary-needle 1052 retracted into housing 101 to prevent auxiliary-needle 1052 from being exposed to housing 101 and causing unnecessary damage.

In the embodiment of the invention, when the slide-buckles 10321 is detached from the limit slot 1015 of the auxiliary-needle, the semi-enclosed needle body 10522 of the auxiliary-needle penetrates the user's subcutaneous.

In the embodiment of the invention, in the installation unit 100, the T-shaped-structure slider 10351 is located in the limit slot 1013, and the limit slot 1013 restricts the position and direction of the parallel slider module 103 through the T-shaped-structure slider 10351 to ensure that the parallel slider module 103 is perpendicular to its sliding direction. Thus, the analyte detection device 104 set at the front end of the parallel slider module 103 is kept perpendicular to its motion direction, and the auxiliary-needle 1052 is kept parallel to its motion direction, so that the part of the sensor inside the auxiliary-needle 1052 and its envelope can pierce the user's skin at a vertical angle to relieve the user's pain.

In the embodiment of the invention, in the process of parallel slider module 103 sliding towards the near end, the T-shaped-structure slider 10351 slides in the limit slot 1013 until it touches the fixed ring 1063 of the triggering module 106. Driven by the first elastic component 1071, the parallel slider module 103 continues to move towards the near end. The fixed ring 1063 stops the T-shaped-structure slider 10351 from moving toward the near end, so the T-shaped-structure slider 10351 is bent around the vertical part, the T-shaped-structure buckle 10352 is disconnected from the buckle hole 10412, and the analyte detection device 104 is separated from the parallel slider module 103, so that it can be installed on the user's skin surface.

In the embodiment of the invention, when the T-shaped-structure slider 10351 contacts with the fixed ring 1063, the position of the parallel slider module 103 is a predetermined position. At this time, the lower-outer-shell 10413 of the analyte detection device contacts the user's skin surface.

In an embodiment of the invention, the auxiliary-needle 1052 passes through the second through-hole and the first through-hole 10414 in turn, and through the analyte detection device 104. Meanwhile, the semi-enclosed needle body 10522 of the auxiliary-needle 1052 envelope sensor 1042. In the process of parallel slider module 103 and auxiliary-needle module 105 moving towards the near end, the semi-enclosed needle body 10522 with sensor 1042 penetrated into the subcutaneous body. After the auxiliary-needle 1052 retracted, the internal part of sensor 1042 remained under the subcutaneous body, and the state of the internal part of sensor 1042 was not affected when the auxiliary-needle 1052 retracted.

In the embodiment of the invention, the user is required to press the housing 101 at the far end and apply force F to the housing 101 at the near end to trigger the fixed ring 1063 of triggering module 106 to contact the user's skin surface, and the user's skin provides force F' of fixed ring 1063 that is opposite to force F, so as to realize the relative movement of triggering module 106 and housing 101. During the actual installation, the absolute position of the triggering module 106 remains unchanged, and the housing 101 moves toward the near end.

Before the installation, in order to prevent the triggering module 106 from moving relative to the housing 101, a protective cover 102 is installed at the near end of the housing 101. The protective cover 102 is surrounded by the fixed ring 1063 of the triggering module 106, so as to prevent the installation action from being carried out in an incorrect position due to the accidental collision of the fixed ring 1063.

At the same time, the auxiliary-needle 1052 and the sensor 1042 are extended into the groove of the inner cover 10233, which can play a sealing role and prevent the outside dust, particles and other dirt from contacting the needle body and the sensor and causing pollution.

In embodiments of the invention, adhesive tape is also arranged on the lower-outer-shell 10413 (not shown in the figure) of the analyte detection device to fix the analyte detection device 104 on the user's skin surface.

To sum up, the invention discloses an installation unit of analyte detection device, which comprises the shell, the protective cover and the label. The protective cover comprises an outer cover and an inner cover. The outer ring of the label is fixed on the near end plane of the outer cover, the inner ring is fixed on the near end plane of the inner cover, and the inner ring of the label is connected with the outer ring through the easy tear seam. Before using the installation unit, the outer cover and inner cover remain fixed relative to the housing. When using the installation unit, the inner cover and inner ring of label remain fixed relative to the housing, and the outer cover and outer ring of label rotate relative to the housing to damage the easy tear seam. After the easy tear seam is damaged, it cannot be restored. The user can judge whether the protective cover of the installation unit has been opened through the state of the easy tear seam, so as to avoid using the contaminated analyte detection device.

Although some specific embodiments of the invention have been detailed through examples, technicians in the field should understand that the above examples are for illustrative purposes only and are not intended to limit the scope of the invention. Persons skilled in the field should understand that the above embodiments may be modified without departing from the scope and spirit of the present invention. The scope of the invention is limited by the attached claims.

The invention claimed is:

1. An installation unit of analyte detection device, which comprises:

a protective cover, comprising an outer cover and an inner cover, wherein the outer cover comprises a first near end plane, and the inner cover comprises a second near end plane;

a label, which comprises an inner ring and an outer ring, wherein the inner ring is fixed on the second near end plane of the inner cover, and the inner ring and the outer ring are connected through an easy tear seam; and a housing, wherein before using an installation unit, the protective cover is fixedly connected with the housing, wherein when using the installation unit, the inner cover remains stationary relative to the housing, the outer cover rotates relative to the housing to damage the easy tear seam at the same time.

2. According to the installation unit of analyte detection device of claim 1, wherein the housing is provided with at least one chute, correspondingly, the outer cover is provided with a bump, which rotates into or out of the chute.

3. According to the installation unit of analyte detection device of claim 2, wherein when the bump rotates into the chute, the outer cover is fixed with the housing, when the bump rotates out of the chute, the outer cover is separated from the housing.

4. According to the installation unit of analyte detection device of claim 3, wherein a triggering module is also fixed in the housing, and at least one fixed groove is arranged on the triggering module, correspondingly, the inner cover is provided with a rib, before using the installation unit, the rib is located in the fixed groove.

5. According to the installation unit of analyte detection device of claim 4, wherein the outer cover is also provided with at least one punctate bulge, and the inner cover is also provided with a annular bulge, which is located between the punctate bulge and the first near end plane of the outer cover.

6. According to the installation unit of analyte detection device of claim 5, wherein a number of the at least one punctate bulge is at least two, the punctate bulges are symmetrically distributed on the outer cover.

7. According to the installation unit of analyte detection device of claim 6, wherein a number of the at least one punctate bulge is three, an angle between two adjacent ones of the punctate bulges is 120°.

8. According to the installation unit of analyte detection device of claim 4, wherein a number of the at least one fixed grooves is at least two, the fixed grooves are symmetrically distributed on the triggering module.

9. According to the installation unit of analyte detection device of claim 8, wherein a number of the at least one fixed groove is three, an angle between two adjacent ones of the fixed grooves is 120°.

10. According to the installation unit of analyte detection device of claim 2, wherein a number of the at least one chutes is at least two, the chutes are symmetrically distributed on the housing.

11. According to the installation unit of analyte detection device of claim 10, wherein a number of the at least one chute is three, with the interval an angle between two adjacent ones of the chutes is 120°.

12. According to the installation unit of analyte detection device of claim 1, wherein the label is made of paper or plastic.

* * * * *